United States Patent
Fok

(10) Patent No.: US 10,493,255 B2
(45) Date of Patent: Dec. 3, 2019

(54) TATTOO NEEDLE

(71) Applicant: Lap Ming Fok, Hong Kong (CN)

(72) Inventor: Lap Ming Fok, Hong Kong (CN)

(*) Notice: Subject to any disclaimer, the term of this patent is extended or adjusted under 35 U.S.C. 154(b) by 265 days.

(21) Appl. No.: 15/656,448

(22) Filed: Jul. 21, 2017

(65) Prior Publication Data

US 2019/0022366 A1    Jan. 24, 2019

(51) Int. Cl.
*A61B 17/34*    (2006.01)
*A61M 37/00*    (2006.01)

(52) U.S. Cl.
CPC .............................. *A61M 37/0084* (2013.01)

(58) Field of Classification Search
CPC ............ A61B 17/3417; A61B 17/3496; A61B 2019/481; A61B 17/34; A61M 37/00; A61M 37/0076; A61M 37/0084
See application file for complete search history.

(56) References Cited

U.S. PATENT DOCUMENTS

2014/0163664 A1* 6/2014 Goldsmith ....... A61B 17/00491
623/1.11

* cited by examiner

*Primary Examiner* — Vi X Nguyen
(74) *Attorney, Agent, or Firm* — Maier & Maier, PLLC

(57) ABSTRACT

Disclosed is a tattoo needle nozzle with rounded silicone rubber grains. The rounded silicone rubber grains are placed in the space between the outer and inner walls of the nozzle to stabilize tattoo needle in operation in order to reduce tattoo pain, and enhance the levels of precision and clarity of tattoo designs.

1 Claim, 1 Drawing Sheet

TATTOO NEEDLE

TECHNICAL FIELD

The utility model relates to a tattoo appliance, and more particularly to a tattoo needle.

BACKGROUND ART

The existing tattoo needle is generally composed of a grip and a tattoo needle nozzle which is fixedly connected inside the grip and is connected to a tattoo ink source and a pushing mechanism. An operate holds the grip to fix the tattoo needle in its entirety and pushes the tattoo needle nozzle forwards to penetrate by means of the pushing mechanism for tattooing. Typically, the tattoo needle nozzle realizes automatic reset of a tattoo needle locking groove by providing a spring outside the tattoo needle locking groove. At present, the connecting between a tattoo needle nozzle and a grip is generally a threaded connection. When the tattoo needle nozzle is to be installed into the grip, the tattoo needle nozzle needs to be screwed into the grip, which is not direct enough and affects the speed of assembling and displacing the tattoo needle nozzle.

SUMMARY OF THE UTILITY MODEL

In view of the deficiencies of the prior art, the utility model aims to provide a tattoo needle adopting a snap-type fixing method, and it requires only to press an outer jacket in order to remove the tattoo needle nozzle from the grip, which is convenient and fast.

In order to achieve the above object, the utility model adopts the following technical solution:

A tattoo needle comprising a grip and a tattoo needle nozzle fixed in an inner cavity of the grip, wherein the inner cavity of the grip is provided with an engagement switch; the bottom of a front end of the engagement switch is provided with engaging protrusions, and the top of the front end is spaced apart from an inner cavity wall of the grip while a rear end of the engagement switch contacts with the inner cavity wall of the grip; the front end and the rear end of the engagement switch can both move upwards and downwards; and a corresponding position at an external top part of the tattoo needle nozzle is provided with engaging recesses that match the engaging protrusions.

Further, the grip comprises an outer jacket and an inner jacket. There is an interlayer between the outer jacket and the inner jacket, there is an indentation at the front end of the interlayer. The rear end of the engagement switch is located within the interlayer and is provided with a space for moving upwards and downwards, while the front end of the engagement switch extends out of the interlayer.

Further, the front end of the engagement switch is fitted with a C-shaped pressure spring, and the C-shaped pressure spring generates pressure on the front end of the engagement switch.

Further, the tattoo needle nozzle comprises an outer sleeve and a tattoo needle receiving recess which are movably connected inside the outer sleeve. Rounded silicone rubber grains are provided between the tattoo needle receiving recess and the outer sleeve. An outer wall of the tattoo needle receiving recess and an inner wall of the outer sleeve are respectively provided with recesses that match the top or the bottom of the rounded silicone rubber grains at corresponding positions. Both the top and the bottom of the rounded silicone rubber grains can be movably embedded into the concave parts of the outer wall of the tattoo needle receiving recess and the inner wall of the outer sleeve. The beneficial effect of the utility model is as follows: by adopting a snap-type fixing method, it requires only to press an outer jacket in order to realize the removal of the tattoo needle nozzle from the grip, which is convenient and fast.

DETAILED DESCRIPTION OF EMBODIMENTS

In the following, the present utility model will be described in detail with reference to the accompanying drawings. Based on this technical solution, the following embodiment provides detailed implementations and specific operation processes. However, it should be noted that the scope of the utility model is not limited to this embodiment.

Figure 1:
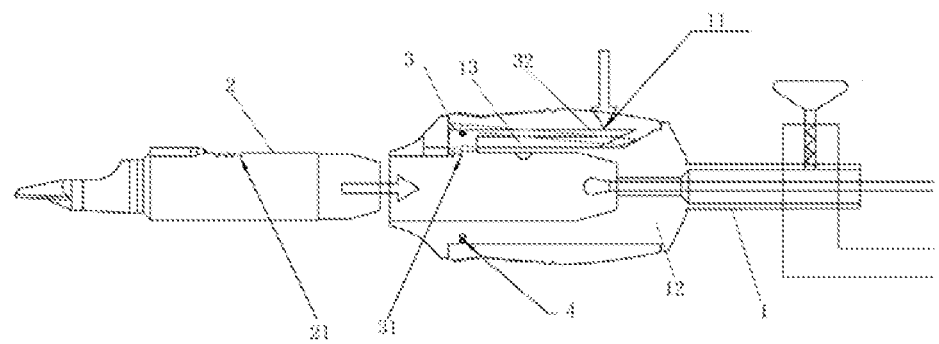
FIG. 1 is a schematic diagram of an overall structure of the utility model.
Figure 2:
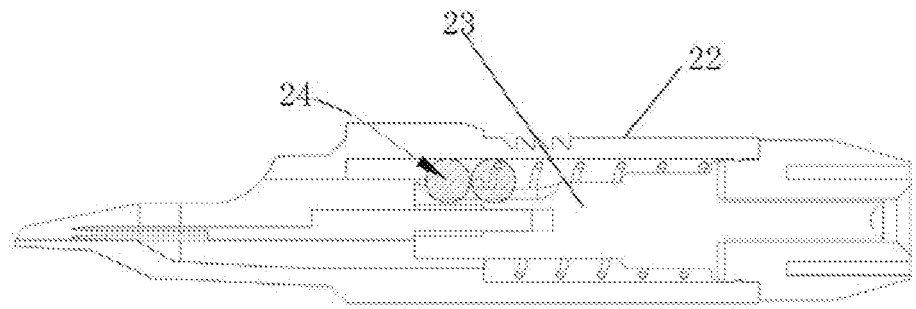
FIG. 2 is a schematic view of a cross section structure of a tattoo needle nozzle in FIG. 1.
Figure 3:
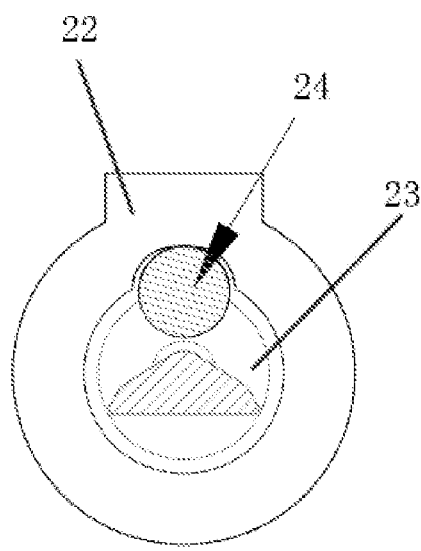
FIG. 3 is a schematic view of a longitudinal section structure of the tattoo needle nozzle in FIG. 1.

As shown in FIGS. 1-3, depicted is a tattoo needle comprising a grip 1 and a tattoo needle nozzle 2. The tattoo needle nozzle 2 is fixed in an inner cavity of the grip 1. The inner cavity of the grip 1 is provided with an engagement switch 3. The bottom of a front end of the engagement switch 3 is provided with engaging protrusions 31, and the top of the front end is spaced apart from an inner cavity wall of the grip 1, while a rear end 32 of the engagement switch 3 contacts with the inner cavity wall of the grip 1. The front end and the rear end of the engagement switch 3 can both move upwards and downwards. A corresponding position at an external top part of the tattoo needle nozzle 2 is provided with engaging recesses 21 that match the engaging protrusions 31.

Further, the grip 1 comprises an outer jacket 11 and an inner jacket 12. There is an interlayer 13 between the outer jacket 11 and the inner jacket 12, there is an indentation at the front end of the interlayer 13. The rear end 32 of the engagement switch 3 is located within the interlayer 13 and is provided with a space for moving upwards and downwards, while the front end of the engagement switch 3 extends out of the interlayer 13.

Further, the front end of the engagement switch 3 is fitted with a C-shaped pressure spring 4, and the C-shaped pressure spring 4 generates pressure on the front end of the engagement switch.

Further, the tattoo needle nozzle 2 comprises an outer sleeve 22 and a tattoo needle receiving recess 23 which are movably connected inside the outer sleeve 22. Rounded silicone rubber grains 24 are provided between the tattoo needle receiving recess 23 and the outer sleeve 22. An outer wall of the tattoo needle receiving recess 23 and an inner wall of the outer sleeve 22 are respectively provided with recesses that match the top or the bottom of the rounded silicone rubber grains 24 at corresponding positions. Both the top and the bottom of the rounded silicone rubber grains 24 can be movably embedded into the concave parts of the outer wall of the tattoo needle receiving recess 23 and the inner wall of the outer sleeve 22.

To those skilled in the art, various changes and modifications may be made in accordance with the above technical solutions and concepts, and all such changes and modifications are intended to be included within the scope of protection of the present utility model.

The invention claimed is:

1. A tattoo needle comprising a grip and a tattoo needle nozzle fixed in an inner cavity of the grip, characterized in that the inner cavity of the grip is provided with an engagement switch; the bottom of a front end of the engagement switch is provided with engaging protrusions, and the top of the front end is spaced apart from an inner cavity wall of the grip, while a rear end of the engagement switch contacts with the inner cavity wall of the grip; the front end and the rear end of the engagement switch can both move upwards and downwards; and a corresponding position at an external top part of the tattoo needle nozzle is provided with engaging recesses that match the engaging protrusions; wherein that the tattoo needle nozzle comprises an outer sleeve and a tattoo needle receiving recess; wherein rounded silicone rubber grains are provided between the tattoo needle receiving recess and the outer sleeve; an outer wall of the tattoo needle receiving recess and an inner wall of the outer sleeve are respectively provided with recesses that match the top or the bottom of the rounded silicone rubber grains at corresponding positions; and both the top and the bottom of the rounded silicone rubber grains can be movably embedded into the concave parts of the outer wall of the tattoo needle receiving recess and the inner wall of the outer sleeve.

\* \* \* \* \*